US00PP21418P3

(12) United States Plant Patent
Bourne

(10) Patent No.: US PP21,418 P3
(45) Date of Patent: Oct. 26, 2010

(54) ***DIANTHUS* PLANT NAMED 'WP08 NIK03'**

(50) Latin Name: *Dianthus×hybrida*
Varietal Denomination: WP08 NIK03

(76) Inventor: Carolyn Grace Bourne, Houndspool, Ashcombe Road, Dawlish, Devon (GB) EX7 0QP ( * ) Notice: Subject to any disclaimer, the term of this patent is extended or adjusted under 35 U.S.C. 154(b) by 0 days.

(21) Appl. No.: 12/456,989

(22) Filed: Jun. 24, 2009

(65) Prior Publication Data

US 2009/0328265 P1 Dec. 31, 2009

(51) Int. Cl.
*A01H 5/00* (2006.01)

(52) U.S. Cl. ..... Plt./282

(58) Field of Classification Search ..... Plt./282
See application file for complete search history.

*Primary Examiner*—Annette H Para

(57) ABSTRACT

A new cultivar of *Dianthus* plant named 'WP08 NIK03' that is characterized by extremely compact habit and early-blooming large fully double magenta-colored flowers. In combination these traits set 'WP08 NIK03' apart from all other existing varieties of *Dianthus* known to the inventor.

2 Drawing Sheets

Genus: *Dianthus.*
Species: ×*hybrida.*
Denomination: 'WP08 NIK03'.

BACKGROUND OF THE INVENTION

The present invention relates to a new and distinct cultivar of hardy garden pink or carnation that is grown for use as a flowering plant for pots and containers and for planting in the garden or landscape. The new cultivar is known botanically as *Dianthus×hybrida* and will be referred to hereinafter by the cultivar name 'WP08 NIK03'.

'WP08 NIK03' is a complex hybrid plant that is the product of a breeding program started by the inventor in 1985. The breeding program is conducted in a cultivated area of Houndspool, Dawlish, Devon, United Kingdom. The inventor selected 'WP08 NIK03' in 2003 for its extremely compact habit and its early-blooming large fully double magenta-colored flowers.

'WP08 NIK03' resulted from the controlled pollination between two unreleased and unpatented varieties, namely *Dianthus* code number ASH21 as female parent plant and *Dianthus* code number 99.24 as male parent plant.

'WP08 NIK03' is distinguishable from the female parent as follows: The female parent has semi-double carmine flowers.

'WP08 NIK03' is distinguishable from the male parent as follows: The male parent is taller in height and bears only single flowers which are colored pink.

The variety of *Dianthus* which is considered by the inventor to most closely resemble 'WP08 NIK03' is the inventor's variety *Dianthus* 'DEVON PP11' (U.S. Plant Pat. No. 14,919). 'WP08 NIK03' is distinguishable from 'DEVON PP11' as follows: 'WP08 NIK03' is shorter than 'DEVON PP11' whose flowers are semi-double and lavender colored.

Asexual reproduction of the new cultivar was first accomplished by the inventor in 2003 in a cultivated area of Houndspool, United Kingdom. The method of asexual propagation used was vegetative cuttings. Since that time the characteristics of the new cultivar have been determined stable and are reproduced true to type in successive generations.

SUMMARY OF THE INVENTION

The following traits have been repeatedly observed and represent the characteristics of the new *Dianthus* cultivar 'WP08 NIK03'. These traits in combination distinguish this cultivar from all other commercial varieties known to the inventor. 'WP08 NIK03' has not been tested under all possible conditions and phenotypic differences may be observed with variations in environmental, climatic and cultural conditions, however, without any variance in genotype.

1. *Dianthus* 'WP08 NIK03' exhibits an extremely compact habit. At 9 months of age, the height of the foliage mound of *Dianthus* 'WP08 NIK03' is 10 cm to 14 cm, and the width of the plant is 13 cm to 15 cm.
2. *Dianthus* 'WP08 NIK03' blooms early and profusely from March until October.
3. *Dianthus* 'WP08 NIK03' bears fully double magenta colored flowers.
4. *Dianthus* 'WP08 NIK03' exhibits grey-green foliage.
5. *Dianthus* 'WP08 NIK03' is perennial and is hardy to −15° C.
6. *Dianthus* 'WP08 NIK03' is suitable for use as a flowering plant in pots and containers.

BRIEF DESCRIPTION OF THE DRAWINGS

The accompanying color drawings illustrate the overall appearance of the new *Dianthus* variety 'WP08 NIK03' showing colors as true as it is reasonably possible to obtain in colored reproductions of this type. Colors in the drawings may differ from the color values cited in the detailed botanical description, which accurately describe the actual colors of the new variety 'WP08 NIK03'.

The drawing labeled as FIG. 1 depicts an entire flowering plant.

Figure 1:
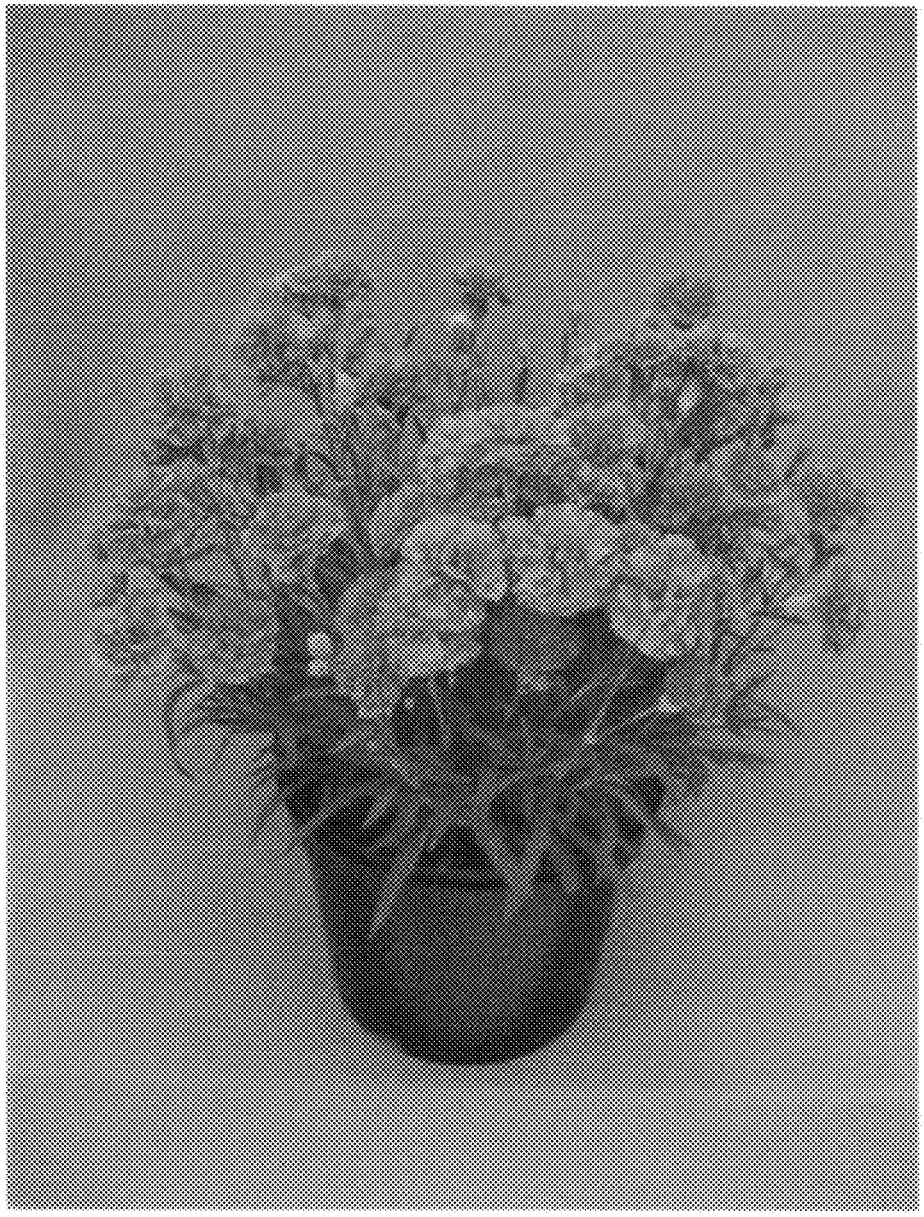
Figure 2:
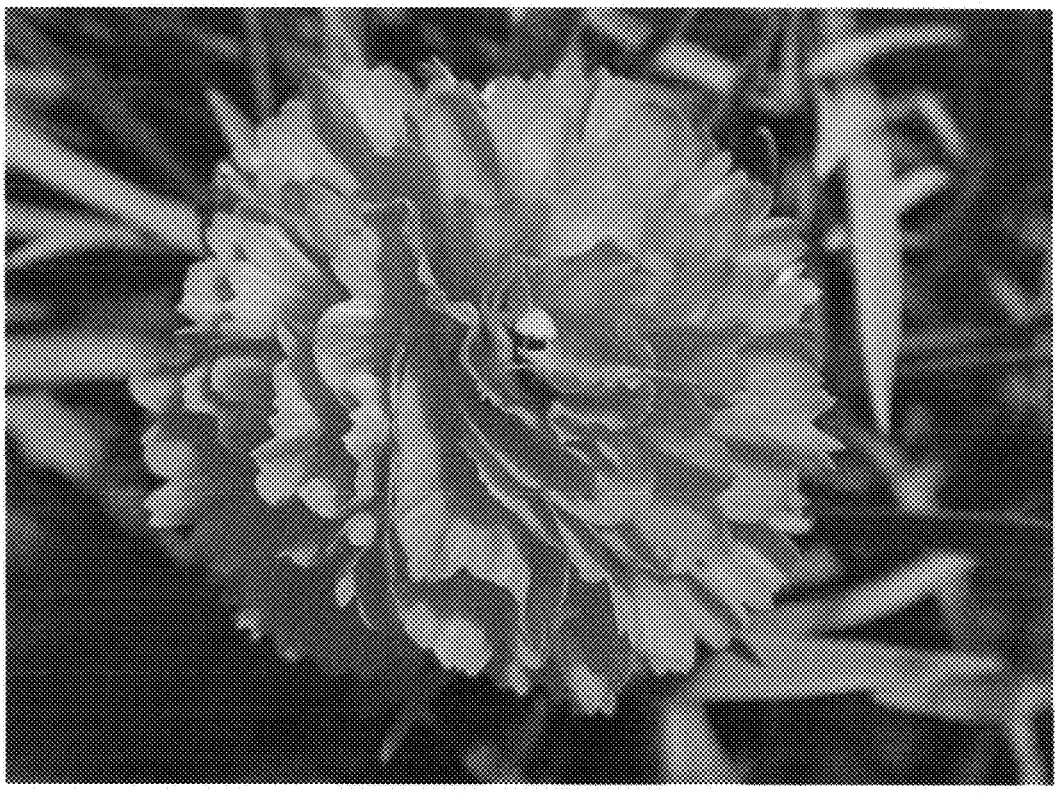

The drawing labeled as FIG. 2 depicts a close-up view of the flower.

All drawings were made of 9 months old plants which have been grown in 1.5-liter containers in a cold glasshouse in Devon, United Kingdom. No chemicals were used to treat the plants. All drawings were made using conventional techniques and although colors may appear different from actual colors due to light reflectance they are as accurate as possible by conventional photography.

DETAILED BOTANICAL DESCRIPTION OF THE PLANT

The following is a detailed description of the new cultivar 'WP08 NIK03'. Data was collected in spring from 1.5-liter container plants in spring, and grown indoors in Devon, United Kingdom. The color determinations are in accordance with the 2007 edition of The Royal Horticultural Society Colour Chart of The Royal Horticultural Society, London, England, except where general color terms of ordinary dictionary significance are used. The colors of stems, leaves, calyx, and epicalyx have been noted on plants which retain the characteristic waxy bloom of *Dianthus*. No chemicals were used to treat the plants. Growing conditions are typical to other *Dianthus*.

Botanical classification:
- *Family.*—Caryophyllaceae.
- *Genus.*—*Dianthus.*
- *Species.*—×*allwoodii.*
- *Denomination.*—'WP08 NIK03'.

Parentage: A complex *Dianthus* hybrid whose immediate parents are unreleased hybrids from the inventor's breeding program, identified as follows:
- *Male parent.*—Selection 99.24.
- *Female parent.*—Selection ASH21.

Plant type: Flowering perennial.

Use of plant: As a flowering plant in containers, window boxes, planters, pots and the garden.

Bloom period: March-October.

Plant habit: A compact mound with many branches and stems upright.

Height of plant: 10 to 14 cm after 9 months.

Width of plant: 13 to 15 cm after 9 months.

Hardiness: Has survived in temperatures of minus 15 Centigrade, equivalent to USDA Hardiness Zone 7. Further hardiness trials continue and may indicate even greater cold tolerance.

Type: Perennial herb.

Root system: Many fibrous roots.

Propagation method: By vegetative stem cuttings.

Cultural requirements: Grow in full sun, in well drained and moderately fertile soil, keep well fertilized and watered.

Diseases and pests: No particular resistance or susceptibility to *Dianthus* diseases and pests are known to the inventor.

Time to root cuttings: 5 weeks is required to produce roots on a vegetative cutting.

Temperature for rooting: A minimum of 15° C. air temperature and 21° C. base temperature at root level is required to produce roots on the cuttings.

Facilities for rooting: A mist propagation unit is required for satisfactory rooting of cuttings.

Crop time: 3 months starting in the Spring and 6 months in the Fall.

Plant stem:
- *Shape.*—Cylindrical.
- *Height.*—5 to 7 cm.
- *Diameter.*—2 to 3 mm.
- *Surface.*—Glabrous and glaucous.
- *Color.*—145C to 145D.
- *Branching.*—Numerous shoots from the axils of the lower leaves.
- *Internode length* (*between nodes*).—8 to 12 mm.

Node:
- *Diameter.*—2 to 3 mm.
- *Length.*—2 mm.

Leaf:
- *Type.*—Evergreen.
- *Shape.*—Linear, straight.
- *Division.*—Simple.
- *Apex.*—Acute.
- *Base.*—Decurrent.
- *Venation.*—Not prominent.
- *Margins.*—Entire.
- *Arrangement.*—Opposite and spiraling on stem.
- *Attachment.*—Sheathing.
- *Surface adaxial.*—Glaucous.
- *Surface abaxial.*—Glaucous.
- *Fragrance.*—Absent.
- *Dimensions.*—Length: 55 mm to 65 mm. Width: 6 mm to 7 mm.
- *Color.*—Adaxial surface: N138B. Abaxial surface: N138C.

Inflorescence:
- *Flower stem dimension.*—Length: 10 cm to 12 cm. Width: 2 mm to 4 mm. Stem strength: Erect. Stem color: 189B.
- *Type.*—Cymose.
- *Form.*—Salviform, symmetrical.
- *Development.*—Singly, in sequence from the uppermost bud.

Buds:
- *Color.*—191B.
- *Dimensions.*—15 mm in length and 9 mm in width.
- *Shape.*—Cylindrical.

Flowers:
- *Number.*—4 to 6 per stem.
- *Dimensions.*—Length (including calyx): 30 mm to 35 mm. Diameter: 40 mm to 48 mm.
- *Flower shape.*—Circular.
- *Flower profile.*—Concave to convex.
- *Lastingness.*—10 days at 20° C., on or off the plant.
- *Fragrance.*—Slight.
- *Flowering period.*—March to October (unforced).

Corolla:
- *Shape* (*upper part of corolla*).—Convex.
- *Shape* (*lower part of corolla*).—Concave.
- *Petal arrangement.*—Persistent, double, overlapping.
- *Petal margin.*—Crenate to dentate.
- *Indentation.*—0 mm to 1 mm deep.
- *Petal texture.*—Soft.
- *Flower type.*—Double.
- *Petal number.*—30 to 40 with a further 15 to 20 petaloid stamens.
- *Petal dimension.*—Length: 32 mm to 34 mm. Width: 20 mm to 22 mm.
- *Color pattern.*—Uniform self-colored throughout.
- *Color of upper surface.*—Ground color of blade: 61C to 64C. Color of middle of strap (basal attachment): 145C. Color of base of strap: 145D.
- *Color of lower surface.*—Ground color of blade: 64C. Color of middle of strap: 145C. Color of base of strap: 145D.
- *Petal shape.*—Obovoid.
- *Petal surface.*—Glabrous and undulating.

Calyx:

*Shape.*—Cylindrical.

*Longitudinal profile.*—Convex.

*Dimensions.*—Length: 16 to 19 mm. Diameter: 10 to 12 mm.

*Sepals.*—Fused.

*Sepals number.*—5.

*Sepals color.*—N138B on the top and 145B on the base.

*Anthocyanin.*—Present, evident in edges of lobes and whole calyx.

*Splitting.*—Yes.

Epicalyx:

*Bracts number.*—1 pair of 2.

*Shape of outer lobe.*—Acute.

*Dimensions.*—Width: 7 mm. Length: 8 mm.

*Color.*—N138A at apex, 142C elsewhere.

*Anthocyanin.*—Present, but absent at apex.

Bracteoles:

*Number.*—1 pair of 2.

*Dimensions.*—Width: 8 mm. Length: 8 mm.

*Color.*—N138A at apex, 142C elsewhere.

*Anthocyanin.*—Present, but absent at apex.

Reproductive organs:

*Stamens.*—Number: 10 to 15, with additional 15 to 20 petaloid or deformed stamens. Color of filaments: White. Dimensions: Length: 18 to 24 mm. Diameter: 0.5 mm.

*Anthers.*—Number: 10 to 15. Color: 84C. Dimensions: Length: 3 mm. Diameter: 2 mm. Attachment: Basifixed.

*Pollen.*—Present occasionally.

*Pollen color.*—157A.

*Style.*—Number: 2. Color: N66D.

*Dimensions* (*style and stigma*).—Length: 19 to 20 mm. Width: 0.5 to 1 mm.

*Stigma.*—Number: 2 (one stigma per style). Color: N66D. Dimensions: N/R.

*Ovary.*—Position: Superior. Dimensions: Length: 9 to 7 mm. Diameter: 4 to 6 mm. Shape: Spindled. Color upper: 145B. Color lower: 145C.

*Seed.*—Not observed.

The invention claimed is:

1. A new and distinct cultivar of *Dianthus* plant named 'WP08 NIK03' as described and illustrated herein.

* * * * *